(12) United States Patent
Metcalfe et al.

(10) Patent No.: US 9,101,548 B2
(45) Date of Patent: Aug. 11, 2015

(54) IMMUNO-MODULATORY COMPOSITION (76) Inventors: Susan Marie Metcalfe, Cambridge (GB); Tarek M. Fahmy, New Haven, CT (US)

( * ) Notice: Subject to any disclaimer, the term of this patent is extended or adjusted under 35 U.S.C. 154(b) by 705 days.

(21) Appl. No.: 12/739,357

(22) PCT Filed: Oct. 24, 2008

(86) PCT No.: PCT/GB2008/003626
§ 371 (c)(1),
(2), (4) Date: May 19, 2010

(87) PCT Pub. No.: WO2009/053718
PCT Pub. Date: Apr. 30, 2009

(65) Prior Publication Data
US 2010/0310639 A1  Dec. 9, 2010

(30) Foreign Application Priority Data
Oct. 26, 2007  (GB) .................. 0721081.8

(51) Int. Cl.
*A61K 38/17* (2006.01)
*A61K 38/19* (2006.01)
*A61K 39/395* (2006.01)
*A61K 9/51* (2006.01)
*A61K 9/127* (2006.01)
*A61K 47/48* (2006.01)
*B82Y 5/00* (2011.01)

(52) U.S. Cl.
CPC .............. *A61K 9/5153* (2013.01); *A61K 9/127* (2013.01); *A61K 47/48823* (2013.01); *A61K 47/48869* (2013.01); *B82Y 5/00* (2013.01)

(58) Field of Classification Search
CPC ..... A61K 9/5153; A61K 38/17; A61K 38/19; A61K 38/2093; A61K 39/395
USPC ................ 424/417, 489; 514/2; 530/351
See application file for complete search history.

(56) References Cited

U.S. PATENT DOCUMENTS

2002/0128179 A1  9/2002  Tacon et al.

FOREIGN PATENT DOCUMENTS

| WO | 9927950 | 6/1999 | |
|---|---|---|---|
| WO | 0164239 | 9/2001 | |
| WO | 0215877 | 2/2002 | |
| WO | 2005051305 | 6/2005 | |
| WO | WO 2005/074973 | * 8/2005 | .............. A61P 37/02 |
| WO | 2005122734 | 12/2005 | |
| WO | 2006080951 | 8/2006 | |

OTHER PUBLICATIONS

Phillips et al, Cancer Detect. Prev. 14(3):383-390, 1990.*
Kaur et al, J. Biol. Chem. www.jbc.org/cgi/doi/10.1074/jbc.M110.179663; published online Feb. 22, 2011.*
Piccinni et al, Eur. J. Immunol. 31:2431-2437, 2001.*
Akita S. et al., "Leukemia Inhibitory Factor Gene Improves Skin Allograft Survival in the Mouse Model," Transplantation (2000) 70:7:1026-1031.
Aluvihare V. et al., "The Role of Regulatory T Cells in Alloantigen Tolerance," Immunol Rev. (2006) 212:330-343.
Berry M.F. et al. "Targeted Overexpression of Leukemia Inhibitory Factor to Preserve Myocardium in a Rat Model of Postinfarction Heart Failure," J Thorac Cardiovasc Surg. (2004)128:866-875.
Chen Z.K. et al., "Amplification of Natural Regulatory Immune Mechanisms for Transplantation Tolerance," Transplantation (1996) 62:9:1200-1206.
Davies J. et al., "'Camelising' Human Antibody Fragments: NMR Sutides on VH Domains," FEB Letters (1994) 339:285-290.
Fahmy T. et al., "Targeted for Drug Delivery," Nanotoday (2005) 18-26.
Fahmy T. et al., "Surface Modification of Biodegradable Polyesters with Fatty Acid Conjugates for Improved Drug Targeting," Biomaterials (2005), 26:5727-5736.
Fahmy T. et al., "Nanosystems for Simultaneous Imaging and Drug Delivery to T Cells," AAPS J. (2007) 9:2:E171-E180.
Gao W. et al., "Treg versus Th17 Lymphocyte Lineages are Cross-Regulated by LIF versus IL-6," Cell Cycle (2009) 8:9:1444-1450.
Ghahroudi M. A. et al., "Selection and Identification of Single Domain Antibody Fragments from Camel Heavy-Chain Antibodies," FEBS Letters, (1997) 414:521-526.
Hamers-Casterman C. et al., "Naturally Occurring Antibodies Devoid of Light Chains," Nature (1993) 363:446-448.
Hilton et al., "Clearance and Fate of Leukemia-Inhibitory Factor (LIF) Ffter Injection into Mice," J Cell Physiol. (1991) 148:3:430-439.
Hori S. et al., "Control of Regulatory T Cell Development by the Transcription Factor Foxp3," Science (2003) 299:5609:1057-1061.
Metcalfe S. et al., "Leukemia Inhibitory Factor Is Linked to Regulatory Transplantation Tolerance," Transplantation (2005) 79:6:726-30.
Metcalfe, S. et al., "Leukaemia Inhibitory Factor (LIF) is Functionally Linked to Axotrophin and Both LIF and Axotrophin are Linked to Regulatory Immune Tolerance," FEBS Letters (2009) 579:609-614.

(Continued)

*Primary Examiner* — Kevin Hill
(74) *Attorney, Agent, or Firm* — Michael Best & Friedrich LLP (57) ABSTRACT

A composition for modulating the immune response in a mammal comprising a pharmaceutically acceptable carrier solution and a plurality of biodegradable nanoparticles, wherein the nanoparticles comprise a targeting moiety that is able to bind selectively to the surface of a T lymphocyte cell and/or of a vascular endothelial cell and wherein the nanoparticles further comprise leukaemia inhibitory factor (LIF). Nanoparticle-mediated targeted delivery of LIF can be used a means to guide tolerogenesis in a patient and has immediate clinical application for recipients of organ grafts and also for patients suffering from autoimmune disease.

3 Claims, 4 Drawing Sheets

(56) References Cited

OTHER PUBLICATIONS

Moran C.S. et al., "Human Leukemia Inhibitory Factor Inhibits Development of Experimental Atherosclerosis," Arterioscler Thromb Vasc. Biol. (1994) 14:1356-1363.

Muthukumarana P. et al., "Evidence for Functional Inter-Relationships Between FOXP3, Leukaemia Inhibitory Factor, and Axotrophin/MARCH-7 in Transplantation Tolerance," Int. Immunopharmacol. (2006) 6:1993-2001.

Muthukumarana P. et al., "Regulatory Transplantation Tolerance and 'Stemness': Evidence that FOXP3 May Play a Regulatory Role in SOCS-3 Gene Transcription," Transplantation (2007) 84:1S:S6-S11.

World C.J. et al., "Regulation of LIF Receptor Expression in Vascular Smooth Muscle," Annals of the New York Academy of Sciences (2001) 947:323-328.

GB Search Report (Application No. GB0721081.8) (Feb. 26, 2008)—4 pages.

International Search Report & Written Opinion (PCT/GB2008/003626) (Aug. 27, 2009)—17 pages.

Park, J. et al., "Modulation of CD4+ T Lymphocyte Lineage Outcomes with Targeted, Nanoparticle-Mediated Cytokine Delivery," Molecular Pharmaceutics, vol. 8, No. 1, pp. 143-152, (2011).

* cited by examiner

No exogenous LIF

|  | 48h |
|---|---|
| "A" genes | |
| LIF-R | 100% |
| TGFb | 100% |
| STAT3 | 100% |
| Sirt-1 | 100% |
| | |
| "B" genes | |
| Cyclin B2 | 100% |
| | |
| "C" genes | |
| LIF | 100% |
| NANOG* | 100% |
| | |
| P53 | 100% |
| H-1 | 100% |
| | |
| "D" genes | |
| SOCS3 | 100% |
| IL6 | 100% |

Exogenous LIF

|  | 48h |
|---|---|
| "A" genes | |
| LIF-R | 95% |
| TGFb | 100% |
| STAT3 | 93% |
| Sirt-1 | 76% |
| | |
| "B" genes | |
| Cyclin B2 | 100% |
| | |
| "C" genes | |
| LIF | 130% |
| NANOG | 190% |
| | |
| P53 | 172% |
| H-1 | 128% |
| | |
| "D" genes | |
| SOCS3 | 44% |
| IL6 | 109% |

Figure 4

IMMUNO-MODULATORY COMPOSITION

CROSS-REFERENCE TO RELATED APPLICATIONS

This application is a national stage filing under 35 U.S.C. 371 of International Application No. PCT/GB2008/003626, filed Oct. 24, 2008, which claims priority benefits to Great Britain Patent Application No. 0721081.8, filed Oct. 26, 2007, both of which are incorporated herein by reference in their entirety.

FIELD

The invention is in the field of compositions for modulating and controlling the immune response in an animal, such as a human. Also concerned are methods for controlling immune response in an animal or in tissues and cells derived from an animal and which are to be utilised in cell and tissue transplantation.

BACKGROUND

Immune-mediated diseases arise when errors occur within the immune system. Normally the immune response carries the potential to destroy foreign antigens whilst at the same time protecting against auto-immune attack. This exquisite ability to discriminate between "self" and "non-self" is orchestrated by the T lymphocytes: these cells ensure destructive aggressive activity only kills foreign targets whilst the immune response to the host ("self") is actively protective and tolerant.

Dominant antigen-specific tolerant T lymphocytes include T regulatory cells ($T_{reg}$), that perform an important role in moderating the immune response in an organism so as to maintain self-tolerance. Cells conforming to the $T_{reg}$ phenotype are a specialized group of T lymphocytes that express cell surface markers including CD4, CD25, CTLA-4, and GITR. $T_{reg}$ cells express the transcription factor Foxp3. Foxp3 functions as a transcriptional repressor required for lymphocyte development down the $T_{reg}$ lineage and loss of Foxp3 function typically results in early death in humans due to the over-whelming auto-immune disease known as IPEX (immunodysregulation polyendocrinopathy enteropathy X-linked syndrome). $T_{reg}$ cells are predominantly derived from the thymus, where they develop under a rigorous process of selection to ensure their self-tolerant reactivity prior to release into wider circulation. Circulating $T_{reg}$ cells contribute to down-regulation of the body's aggressive immune responses against foreign pathogens. $T_{reg}$ cells also dominate and suppress any aggressive immune responses that may otherwise lead to attack of the body's own tissues (i.e. self tolerance).

Disease can ensue when self-tolerant $T_{reg}$ cells become weakened, thereby allowing aggressive cells to break through. In some individuals crippling auto-immune diseases will develop. Such inappropriate immune activity is thought to underly a wide number of diseases that lack curative therapy including rheumatoid arthritis, type I diabetes mellitus, systemic lupus erythematosis (SLE), psoriasis, and Crohn's disease to name a few.

Immune tolerance is also of crucial importance in the field of organ transplantation. There is a critical shortage of donor organs and it is of primary concern that appropriate tissue typing is conducted on the donor tissue and the recipient prior to transplantation. In spite of an apparently good match between a recipient host and a donor, the recipient's immune system will naturally recognize the allografted tissue as 'foreign' and if left uncontrolled will reject the transplant. Consequently, donor organ recipients must remain on immunosuppressive therapy for the remainder of their lives following transplant. Even then, recipients are subject to progressive chronic rejection within the blood vessels of the transplanted organ due to an insidious process that is not controlled by current immunosuppressive drugs: such chronic vascular rejection eventually blocks the blood flow within the transplanted organ causing organ failure. Without a new organ transplant—unlikely given the shortage of organs—or dialysis in the case of kidney graft recipients, the patient will die.

In 2004 around 15,000 kidney transplant procedures were carried out in the US alone, with a one year graft survival rate of around 90% (from OPTN/SRTR Data as of May 1, 2006). Nevertheless, at the filing date of this application over 70,000 people were on the waiting list for a kidney transplant in the US, clearly demonstrating that demand outstrips supply many times over. For other organs the graft survival rate falls, for example the one year survival rate for liver transplants was around 83%, and the demand also is greater than the available supply of donor material. Apparently high graft survival rates often belie the fact that transplantation is often only available for individuals with a highly favorable clinical case. Those patients who are unfortunately regarded as being poorer candidates for transplant will rarely ever become recipients of much needed donor tissue.

There is a need to improve control of the immune response to promote host tolerance to allografted tissue such that host acceptance of transplanted material is increased. In addition, modulation of the immune response in the recipient so as to promote recognition of the foreign transplanted tissue as 'self' may also serve to reduce the dependency on lifelong immunosuppressive therapy. Further, improved immuno-modulatory treatments may also effect the ability to match donor tissue with recipients in need of a transplant, by expanding the parameters for tissue type matching—i.e. by expanding the tolerance parameters for mismatch between the tissue type of the host and that of the donor. This is of primary importance for patients with rare tissue types, such as those from particular ethnic minorities.

The present invention seeks to overcome or at least reduce the problems that exist by providing compositions and methods for targeted modulation of the immune response and promoting proliferation and activity of $T_{reg}$ cells that will suppress the anti-donor response and/or the chronic vascular rejection process. Not only does the targeted mode of delivery bring immune-modulators to the site where they are needed, for example within the organ transplant, but also it reduces the overall exposure of the patient to bio-active components that may carry toxic side-effects at irrelevant sites.

SUMMARY

The invention provides directed therapy specifically to the site of immune activity that is associated with the diseased state. The invention also exploits a novel molecular approach to reduce aggressive immune activity by harnessing the body's own protective mechanism. The clinical benefit is considerable both for patients with autoimmune disease and for organ graft recipients.

A first aspect of the invention provides a composition for modulating the immune response in a mammal comprising:
  a) a pharmaceutically acceptable carrier solution; and
  b) a plurality of biodegradable nanoparticles, wherein the nanoparticles comprise a targeting moiety that is able to bind selectively to the surface of a T lymphocyte cell and/or of a vascular endothelial cell and wherein the nanoparticles further comprise leukaemia inhibitory factor (LIF).

A second aspect of the invention provides a method of inducing a T lymphocyte cell to adopt a $T_{reg}$ phenotype comprising exposing the T lymphocyte to a plurality of biodegradable nanoparticles, wherein the nanoparticles comprise a targeting moiety that is able to bind selectively to the surface of the T lymphocyte cell and/or to a vascular endothelial cell and wherein the nanoparticles further comprise leukaemia inhibitory factor (LIF).

A third aspect of the invention provides a biodegradable nanoparticle comprising a biodegradable carrier material that encapsulates a therapeutic compound, a therapeutic compound, and a surface located targeting moiety, characterised in that the therapeutic compound is LIF and the surface located targeting moiety is an antibody, or an antigen binding fragment of an antibody, that specifically binds to an antigen present on the cell surface of a T lymphocyte and/or of a vascular endothelial cell.

A fourth aspect of the invention provides use of a preparation comprising a plurality of biodegradable nanoparticles, wherein the nanoparticles comprise a targeting moiety that is able to bind selectively to the surface of a T lymphocyte cell and/or of a vascular endothelial cell, and wherein the nanoparticles further comprise leukaemia inhibitory factor (LIF), in the manufacture of a composition for moderating immune response in a patient. Other aspects of the invention provide uses for the treatment of autoimmune disease and graft versus host disease.

A further aspect of the invention provides a method of promoting an immune tolerance response in a patient comprising administering to the patient a therapeutically effective amount of a composition comprising a plurality of biodegradable nanoparticles, wherein the nanoparticles comprise a targeting moiety that is able to bind selectively to the surface of a T lymphocyte cell and/or of a vascular endothelial cell, and wherein the nanoparticles further comprise leukaemia inhibitory factor (LIF).

A further aspect of the invention provides a method of storing mammalian tissue destined for allografting into a recipient comprising perfusing the tissue with a solution that comprises a plurality of biodegradable nanoparticles, wherein the nanoparticles comprise a targeting moiety that is able to bind selectively to the surface of a T lymphocyte cell and/or of a vascular endothelial cell, and wherein the nanoparticles further comprise leukaemia inhibitory factor (LIF).

These and other aspects and embodiments of the invention will become apparent from the detailed description of preferred embodiments of the present invention below.

DRAWINGS

FIG. 2 (a) Shows the results of an experiment in histogram format in which T lymphocytes from axotrophin null mutant mice are treated with LIF and then assayed for release of the pro-inflammatory cytokine interferon gamma (LIF is shown in black the control is shown in hatching). (b) Interferon gamma release is very high in rejection and is partially inhibited by LIF. Release of interferon gamma into the supernatant of primed rejected cultures increased with time, reaching 16 ng/ml at 5 days after reboost with donor antigen; the presence of recombinant LIF suppressed this interferon gamma release by around 50%. In tolerance, interferon gamma never exceeded 200 pmol, with or without LIF.

DETAILED DESCRIPTION

The invention provides nanoparticle-mediated targeted delivery of LIF (leukaemia inhibitory factor) as a novel means to guide tolerogenesis in a patient. The inventors have previously shown that LIF is a key regulator of the immune response in which $T_{reg}$ lymphocytes collectively ensure protective tolerance towards self-tissues whilst simultaneously enabling aggressive attack towards foreign pathogens. Without being bound by theory, the role of LIF in this critical balance is believed to be linked to $T_{reg}$ cells and acts in concert with Foxp3. Sustained LIF activity is an intrinsic feature of $T_{reg}$ cells, supporting the notion that LIF provides a cue for $T_{reg}$ development and $T_{reg}$ maintenance. The present invention utilises LIF-loaded nanoparticles that are specifically targeted to T lymphocytes so as to guide naïve T cells into becoming antigen-specific $T_{reg}$ cells via exposure to high local concentrations of LIF activity. An advantage of this approach is that it has immediate clinical application for recipients of organ grafts and also for patients suffering from autoimmune disease.

According to the present invention modulation of immune tolerance is considered to encompass a suppression of an organism's inherent basal level of immune function. Typically, the organism is an animal, more typically a mammal or a human. The basal level is taken as the level of immune reactivity in the organism prior to treatment with a composition of the invention. In a normal healthy individual, such as a human patient, the immune level would be equivalent to that of an unchallenged steady-state level. Whereas in a patient suffering from an autoimmune disorder the basal immune response would be elevated in comparison with a normal healthy patient. Likewise, in a patient who has recently received allografted tissue, one would expect to see an elevated basal level of immune activity in the absence of immunosuppressive therapy such as cyclosporine. Elevated immune activity can be identified by a relative increase in aggressive killer white blood cells such as neutrophils, macrophages, and cytotoxic T cells, as well as elevated levels of cytokines such as IL-2, IL-6, IL-13, IL-17, IL-23, and inflammatory mediators including interferon-gamma, TNFα and IL1β.

LIF is a member of the IL-6 family of cytokines. It is a secreted signalling factor that binds to and signals via a LIF-specific cell surface receptor gp190 that interacts with the gp130 signal transducing receptor. Downstream intracellular signal propagation occurs via the JAK/STAT pathway, especially via the transcription factor STAT-3. LIF signalling activity is terminated by SOCS3, SOCS3 being induced in a feedback loop mechanism. The present inventors have previously identified that ex vivo treatment of murine spleen cells with LIF increases Foxp3 transcription. Further, in contrast to a mutant FOXP3 that is unable to bind DNA and function as a transcriptional repressor—wild-type FOXP3 strongly inhibits SOCS-3 (suppressor of cytokine signalling-3) (Muthukumarana et al 2007). Since SOCS-3 is a feedback inhibitor of LIF signalling, its repression by wild-type FOXP3 in $T_{reg}$ cells will have a positive effect on LIF activity. In $T_{reg}$ cells LIF signalling activity is also known to be linked to activity of the E3 ligase MARCH VII (axotrophin) which in-turn regulates activity of Foxp3. A hierarchical regulatory cassette between LIF, Foxp3, and axotrophin is envisaged. Given that Foxp3 is considered to be one of the archetypal markers of the $T_{reg}$ phenotype, regulation of LIF activity in the $T_{reg}$ cells and in $T_{reg}$ precursor cells can have a profound effect upon the tolerogenic immune response in an animal.

The pleiotrophic properties of LIF are wide ranging and include the cardiovascular system. Targeted over-expression of LIF in infarcted myocardium prevents myocardial loss and improves post-infarct cardiac function in rats (Berry M F et al. J Thorac Cardiovasc Surg. 2004 December; 128(6):866-75). LIF also displays a multifaceted capacity for treating occlusive vascular disease, particularly at the early stages of atherosclerotic plaque formation (Moran C S et al. Arterioscler Thromb. 1994 August; 14(8):1356-63; World C J et al. Ann N Y Acad Sci. 2001 December; 947:323-8) and LIF gene therapy has been shown to be beneficial for skin allograft survival in mice (Akita S. et al. Transplantation. 2000 Oct. 15; 70(7):1026-31).

In an embodiment, the present invention provides compositions comprising LIF that can be targeted to a location on a cell, within a tissue or within the body of a patient or animal. For example, compositions of the invention can comprise bioavailable LIF that is directed to cells that express the cell surface receptor CD4 (CD4+ cells) and thereby increase localised exposure to LIF for these cells. In another embodiment of the invention LIF can be targeted to cells that express a cell surface biomarker that is characteristic of or associated with pluripotency, such as stage specific embryonic antigen 1 (SSEA-1). Other cell surface expressed molecules that could be targeted by the compositions of the invention include VEGF Receptor, EPCR, CD34 and/or CD31 expressed on vascular endothelial cells to generate a tolerogenic microenvironment within an organ or tissue.

In accordance with the invention, T cells that are uncommitted can be diverted down the path to becoming $T_{reg}$ (self-tolerant) cells by exposure to LIF signalling. LIF cannot be readily administered systemically due to its cytotoxicity and short half-life in vivo. The present invention provides a targeted approach to LIF delivery, which provides the dual advantages of increasing the local concentration of LIF at the point of need (i.e. at the cell surface of the antigen-responsive T cell) and reducing the overall concentration of LIF that is required to obtain the desired therapeutic effect. In a specific embodiment of the invention, LIF containing nanoparticles are targeted at T lymphocytes, in particular T lymphocyte specific markers located on the cell surface. Alternatively, LIF containing nanoparticles are targeted to vascular endothelial cells. Targeting to the specified cell surface marker is typically achieved by locating a targeting moiety, such as antibodies, on the surface of the nanoparticle. Polymer based nanoparticles that comprise antibody targeting moieties are described in WO-A-2006/080951, liposomal nanoparticles that comprise antibody targeting moieties are described in WO-A-2005/051305.

As used herein, the term 'antibody' denotes a protein that is produced in response to an antigen that is able to combine with and bind to the antigen, preferably at a specific site on the antigen, known as an epitope. The term as used herein includes antibodies of polyclonal and monoclonal origin, unless stated otherwise. Polyclonal antibodies are a group of antibodies produced by different B lymphocytes in response to the same antigen; different antibodies in the group typically recognize different parts (epitopes) on the antigen. A monoclonal antibody recognizes only one type of antigen and is produced by the daughter cells of a single antibody-producing lymphocyte, typically a hybridoma. Also included within the term 'antibody' are antigen binding fragments of naturally or non-naturally occurring antibodies, for example, the "Fab fragment", "Fab' fragment" (a Fab with a heavy chain hinge region) and "F(ab')2 fragment" (a dimer of Fab' fragments joined by a heavy chain hinge region). Recombinant methods have been used to generate small antigen-binding fragments, such as "single chain Fv" (variable fragment) or "scFv," consisting of a variable region light chain and variable region heavy chain joined by a synthetic peptide linker. Unlike antibodies derived from other mammals, camelid species express fully functional, highly specific antibodies that are devoid of light chain sequences. Camelid heavy chain antibodies are of particular use, as they are found as homodimers of a single heavy chain, dimerized via their constant regions. The variable domains of camelid heavy chain antibodies are referred to as VHH domains and retain the ability, when isolated as small fragments of the VH chain, to bind antigen with high specificity (Hamers-Casterman et al., 1993, Nature 363: 446-448; Gahroudi et al., 1997, FEBS Lett. 414: 521-526). Further included within the term 'antibody' are so called camelized mutants of human VH domains that retain antigen binding activity but exhibit some of the advantages of camelid VHH domains (Riechmann, 1994, FEBS Lett. 339: 285-290). In addition to antigen binding fragments, antibodies of the present invention can include derivatives of antibodies, such as chimeric fusions with labelling moieties including green fluorescent protein (GFP).

Alternative non-antibody targeting moieties can be utilised to target the nanoparticles of the invention to the cells of choice. For example, affinity labels such as streptavidin can be used to target a biotinylated target. Other suitable affinity labels will be known in the art and can include tethered ligands for a cell surface receptor known to be specifically expressed on the target cell.

In an embodiment of the invention the composition comprises a biodegradable polymer based nanoparticle comprising encapsulated LIF polypeptide, which nanoparticle further comprises surface exposed antibody that specifically binds for example to the CD4 receptor. Suitably, the polymer is a polylactide-co-glycolide polymer (PLG). The nanoparticles of the invention are resuspended in a biocompatible solution, such as phosphate buffered saline, and can be used in vivo (e.g. via parenteral administration), in vitro or ex vivo in order to modulate the immune response. Ex vivo uses can include pre-treatment of donor tissue intended for allografting with the compositions of the invention shortly before implant, thereby improving the chances of acceptance of the allografted tissue by the recipient. In this latter embodiment of the invention, the nanoparticles can comprise an alternative targeting moiety in addition to or in place of the CD4-binding antibody, for example an antibody that targets the endothelial cells present within the allograft tissue. In such a way, LIF can be controllably released from within the allografted tissue in the period immediately after transplant, thereby facilitating the immune tolerance reaction in the recipient.

The compositions of the invention are suitable for the treatment of autoimmune disorders. Local parenteral or subcutaneous delivery of the nanoparticle-comprising compositions of the invention into or around an inflamed joint can assist in amelioration of the symptoms of rheumatoid arthritis. Also, topical administration of an appropriate nanoparticle composition (i.e. as a lotion or skin cream) can be effective in treatment psoriasis. Finally, the nanoparticles can be incorporated into a time release depot formulation for longer term use, suitable for treatment of auto-immune encephalopathies and multiple sclerosis.

The compositions of the invention are useful for the control of immune response in vivo, ex vivo or in vitro. In a specific embodiment of the invention tissues and organs intended for transplantation (e.g. heart, kidney, bone and blood vessel grafts) can be pre-treated with the compositions of the invention prior to implantation into the recipient. Cellular allograft tissue, such as bone marrow or stem cells can also be treated in vitro or ex vivo, prior to introduction into the recipient. As such, the compositions of the invention provide a facilitating technology for the expansion of a variety of regenerative medicine therapies.

In a particular embodiment, nanoparticles of the invention are comprised within the perfusion solution that is used for organ and tissue preservation during transplant of donor organs. In this way, the LIF comprised within the nanoparticles serves a dual purpose of maintaining proliferation of endogenous stem cells within the transplant tissue as well as favouring immune tolerance in the recipient after the transplant procedure has been completed.

Example 1

Experimental models in mice have identified a critical regulatory system in T lymphocytes wherein Foxp3—the master gene for regulatory tolerance—is itself regulated by axotrophin/MARCH-7 (an E3-ligase) and LIF. Not only does axotrophin/MARCH-7 directly regulate LIF release by T lymphocytes, but also both axotrophin/MARCH-7 and LIF are required for normal Foxp3 gene activity.

In humans, Foxp3 and axotrophin/MARCH-7 are co-expressed in peripheral blood cells. In patients who have received a bone marrow transplant, and also in patients who have received a kidney transplant, expression of Foxp3 and axotrophin/MARCH-7 positively correlate with good graft function (Muthukumarana et al 2007). These findings infer that the relationship between immune tolerance, axotrophin/MARCH-7 and—by extrapolation—LIF is valid in clinical patients and supports the present invention which adopts a novel tolerogenic therapeutic approach of targeted delivery of LIF to the site of immune activity.

Reciprocity Between Foxp3 and LIF

TABLE 1

SOCS-3: fold change from 0 h to 24 h after induction of Foxp3 in human T cells

| transcript | Wild-type FOXP3 | DE251 FOXP3 |
|---|---|---|
| SOCS-3 | 12.00 | 345.00 |
| LIF | 64.00 | 0.02 |
| FOXP3* | 9.00 | 10.00 |

*both transcript and protein equivalent

Targeted Drug Delivery Using Nanoparticles

Polymeric biodegradable nanoparticles that combine high drug loading with targeting to specific cell types have been developed by Yale University (see WO-A-2006/080951; and Fahmy et al 2005). LIF-loaded nanoparticles were prepared according to this protocol: these were coated with avidin to permit addition of biotinylated antibody. The present inventors have extended the use of this therapeutic resource to control the immune response for transplant recipients and for patients with auto-immune disease.

In accordance with the present invention, it is considered that LIF is a previously unrecognised regulator of immune tolerance and functions in concert with Foxp3. Accordingly it is proposed that LIF therapy targeted to CD4+ lymphocytes will guide naïve T cells towards the tolerant phenotype ($T_{reg}$).

Experimental Design

Based on clinical, experimental, and molecular data this Example tests a novel therapeutic approach that combines two strategies, namely (i) targeted delivery and (ii) harnessing of natural regulatory pathways.

Interferon Gamma Release is Reduced in Immune Cells Exposed to LIF Treatment

Figure 2:
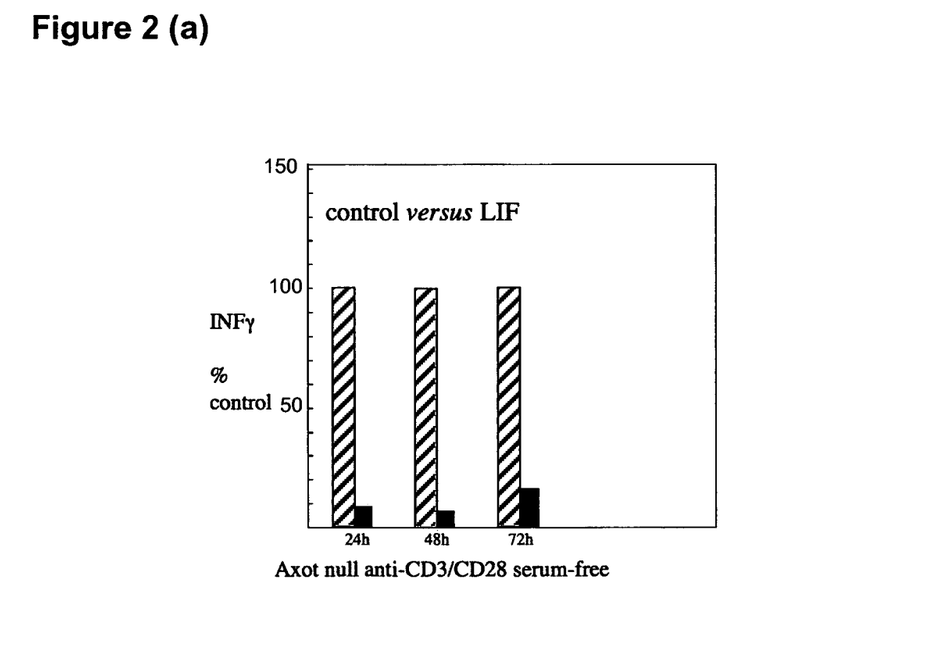

Interferon gamma release is strongly correlated with rejection ex vivo, whilst self-self controls reveal low background levels of interferon gamma. When stimulated by a third party antigen (C57B16) tolerant and rejected cultures of CBA spleen cells from a BALB/c tolerant or rejection mouse model each release high levels of interferon gamma but with slower release kinetics when compared to primed cultures, demonstrating the specificity of the allo-tolerant ex vivo state where interferon gamma is low. When serum-free cell cultures of these cells are treated with LIF the release of interferon gamma in primed rejection is markedly reduced, this being halved from control values of around 9 ng/ml to around 4 ng/ml (FIG. 2 (b)). In primed tolerant cells interferon gamma levels are very low, and largely unresponsive to addition of exogenous LIF. The concentration of released interferon gamma is determined according to ELISA and Western blotting.

The suppressive effect of LIF signalling on interferon gamma release was increased to 90% suppression when naïve spleen cells taken from axotrophin null mutant mice were activated in vitro by CD3/CD28 cross-linking (FIG. 2(a)). This indicates that LIF treatment can leads to suppression of release of the inflammatory cytokine interferon gamma from immune cells in vitro under certain cellular conditions.

LIF Therapy Using Nanoparticles

Figure 1:
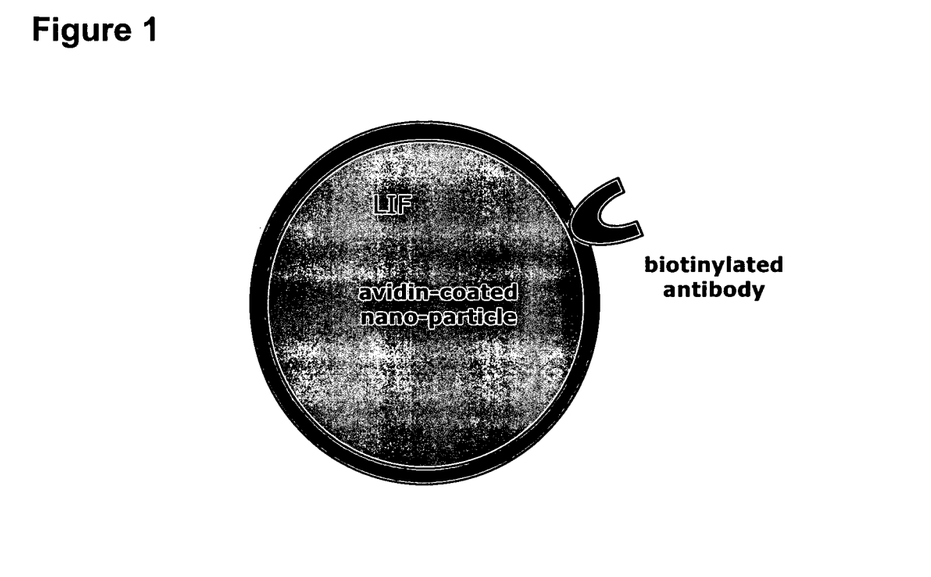
Fig. 1 shows a diagrammatic cross sectional view of an exemplary T lymphocyte or vascular endothelial cell targeted nanoparticle of the invention, wherein the nanoparticle in the construction shown in FIG. 1 is a LIF-loaded, avidin-coated nanoparticle precoated with biotinylated antibody.

Since $T_{reg}$ cells arise from CD4+ T cells the LIF-loaded nanoparticles are precoated with biotinylated-anti-CD4 antibody (as shown in FIG. 1) the aim being to target LIF to the sites of antigen engagement for CD4+ lymphocyte activation. Unloaded nanoparticles act as controls whilst delivered LIF dose is determined by comparison between treated and control supernatants from the in vitro experiments.

The strategy has the additional benefit that nanoparticles may also be phagocytosed by antigen presenting cells, further increasing the delivery of LIF to the micro-environment of the responding lymphocyte. In vivo, tissue uptake of the nanoparticles from blood is measured in all the major organs including lung, liver, kidney, spleen, lymph node, thymus, heart, and brain. Nanoparticle size of <500 nm can reduce sequestration to the liver: should this remain a problem "stealth" nanoparticles can be prepared by including biotinylated poly-ethylene glycol (PEG) in the surface coat.

Foxp3 Measurement by Flow Cytometry

A critical readout for the experiments is expression of Foxp3 protein in CD4+ lymphocytes (see FIG. 2). Standardised flow cytometry protocol employs six colour analyses of single cells in complex populations: accordingly each cell is characterised against 36 potential variables. Surface staining includes for CD4, CD3, CD25, CD8, CTLA-4, and gp190 (the LIF-specific receptor subunit) whilst intracellular staining measures Foxp3 and cytoplasmic CTLA-4. Cell populations are phenotyped at 0h and after culture plus stimulating allo-antigen in the presence or absence of LIF nanoparticles. In accordance with the methods of the present invention, LIF nanoparticle therapy leads to a significant increase in the numbers of Foxp3+ cells.

Three experimental approaches are taken to validate the results further.

(i) Mixed lymphocyte response: An in vitro model of allo-reactivity is the one way mixed lymphocyte response (MLR) and human peripheral blood lymphocytes are used in established MLR protocols to measure both DNA synthesis by tritiated thymidine uptake and expression of Foxp3 by single cell flow cytometric analysis following activation in the presence or absence of LIF therapy. These experiments can identify the effect of LIF during priming to allo-antigen over a 7 day period.

(ii) Primed MLR response: Use of allo-reactive primed lymphocytes asks to what extent can primed donor-specific immune reactivity be guided towards the tolerant state by LIF therapy. Here both human and murine models are used. Human experiments look at peripheral blood lymphocytes following stimulation with commercially available "donor-specific" antigen coated beads followed by re-boosting with beads used in the priming step, or with third-party beads. Parallel ex vivo studies utilise CBA mice grouped into "allo-tolerant" versus "allo-rejected" recipients of a fully mis-matched BALB/c heart allograft: here donor-antigen stimulation is via irradiated BALB/c spleen cells using standard protocols Again it is determined whether LIF-loaded nanoparticles bias the allo-rejected anti-donor response towards tolerance, by looking for increases in Foxp3 positive cell numbers over a 7 day period. Full phenotype profiling occurs at time zero, 3, 5, and 7 days to look for changes as allo-activation progresses.

(iii) In vivo tolerogenesis by LIF therapy: To be able to influence $T_{reg}$ development in vivo, rather than in culture, represents a significantly greater challenge since it is known that recombinant LIF delivered intravenously or into the peritoneum is very rapidly degraded [Hilton et al 1991]. The present inventors have developed a novel approach using targeted nanoparticles that represents a powerful means to achieve LIF delivery direct to the micro-environment of naïve T cells, where slow release will optionally be continuous over several weeks, and the murine heart allograft model is suitable for testing the efficacy of such LIF therapy in vivo, typically as a preliminary to pre-clinical studies.

To test the effect of nanoparticle-encapsulated LIF on heart allograft survival in BALB/c mice receiving a vascularised CBA heart graft the following trial has been devised. Recipient mice receive CD4 targeted nanoparticle-encapsulated LIF (supplied by Tarek Fahmy and Jason Park, Yale University). Historical controls received no therapy and rejected their graft around day 7 post-grafting. The importance of this experiment is the understanding of the regulatory mechanisms that control T cells in vivo.

Materials and Methods

CBA to BALB/c heart grafts day 0: N=2
Micro-encapsulated LIF Preparation:
Pre-zap all inert surfaces to eliminate static charge
6 mg nanoparticles in Eppendorf tube [~6 micrograms LIF] resuspend in 500 microlitres sterile PBS
Add 100 microlitres sterile biotinylated anti-CD4 stock (eBioscience Cat N 36-0041 (13-0041) 0.5 mg in PBS no NHN$_3$:rat IgG2b, k) @1 mg/ml (0.1 mg total)
Incubate at room temperature for 30 minutes
Spin @10,000g for 5 minutes
Keep supernatant
Resuspend nanoparticles vigorously by sonication
WASH :Add slowly 1 ml sterile PBS
Spin @10,000g for 5 minutes
Keep supernatant [~3 micrograms LIF (assuming 50% loss)]
Treatment of Allograft Recipients:
Resuspend the nanoparticle pellet vigorously by sonication
Add slowly—with sonication—400 microlitres sterile PBS
Resuspend vigorously by sonication for intravenous delivery PER MOUSE of 200 microlitres
Treatment is carried out on Day 0; Day 2; Day 4 by introducing 200 microlitres of resuspended LIF nanoparticles into the tail vein using a 27 ½ gauge needle.

At time of rejection (cessation of transplanted heart beat) the animal is culled and the donated heart is removed for analysis. The native heart is also preserved for analysis. Samples are also taken of blood, lung, liver, kidney, skin, thymus, lymph node, brain, large and small intestine to determine nanoparticle distribution and uptake.

Mice

Gene trap insertion was used to generate axotrophin null BALB/c mice and littermates from heterozygous parents were genotyped by PCR analysis of genomic DNA to identify axot+/+, axot+/−, and axot−/− pups as detailed previously. Spleen, thymus and lymph node were obtained from 5 m old littermates and kept on ice prior to cell preparation for the analyses described below. The lymph node tissue yielded very few cells and was discarded Cell Preparations Splenocytes and thymocytes were teased out from each organ and collected in sterile growth medium [RPMI-1640 (Gibco™ Invitrogen Co.) supplemented with 10% FCS (Gibco™ Invitrogen Co.), 200 mM L-Glutamine, 100 U/mL Penicillin and 100 µg/mL Streptomycin (Sigma Chemical Co.)]. The cell suspensions were washed, resuspended in growth medium and counted using a haemocytometer.

ELISA

ELISA's were performed on the 48h culture supernatants, in 96-well Falcon® plates using the DuoSet® ELISAS for Interferon gamma (DY485), IL2 (DY402), IL4 (DY404), (DY417) and Quantikine®M Immunoassay for LIF (MLF00), from R&D Systems. The standard curves were established by processing the optical density data using Microsoft Excel software and cytokine concentrations were determined using the standard curves.

Flow Cytometry

The splenic and thymic cell suspensions were RBC depleted and washed in FACS staining solution (0.2% BSA and 0.1% sodium azide in 1×PBS) prior to being mixed with the various monoclonal antibodies detailed below, these being either directly or indirectly conjugated with Phycoerythrin (PE) or Fluorescein isothiocyanate (FITC). PE-rat anti-mouse CD19 (557399), PE-hamster anti-mouse TCRα chain (553172) and rat anti-mouse dendritic cell clone 33D1 (551776) were from Pharmingen. Rat anti-mouse CD205-FITC (MCA949F), mouse anti-rat IgG2a heavy chain-FITC (MCA278F) and mouse anti-rat IgG2b chain-FITC were from Serotec Ltd. while rabbit anti-mouse CD25 (IL2Rα) and goat anti-rabbit IgG (H&L)-PE (4050-89) were from Santa Cruz Biotechnology and Southern Biotechnology Associates respectively. Anti CD4 (YTS177.9.6) and anti CD8 (YTS105.18.10) were a gift from Professor Stephen Cobbold, University of Oxford. Analyses were performed on a Becton Dickinson FACSCalibur instrument equipped with CellQuest software.

Example 2

This Example shows the effect of exogenous LIF on T cells activated by CD3/CD8 ligation.

Figure 3:
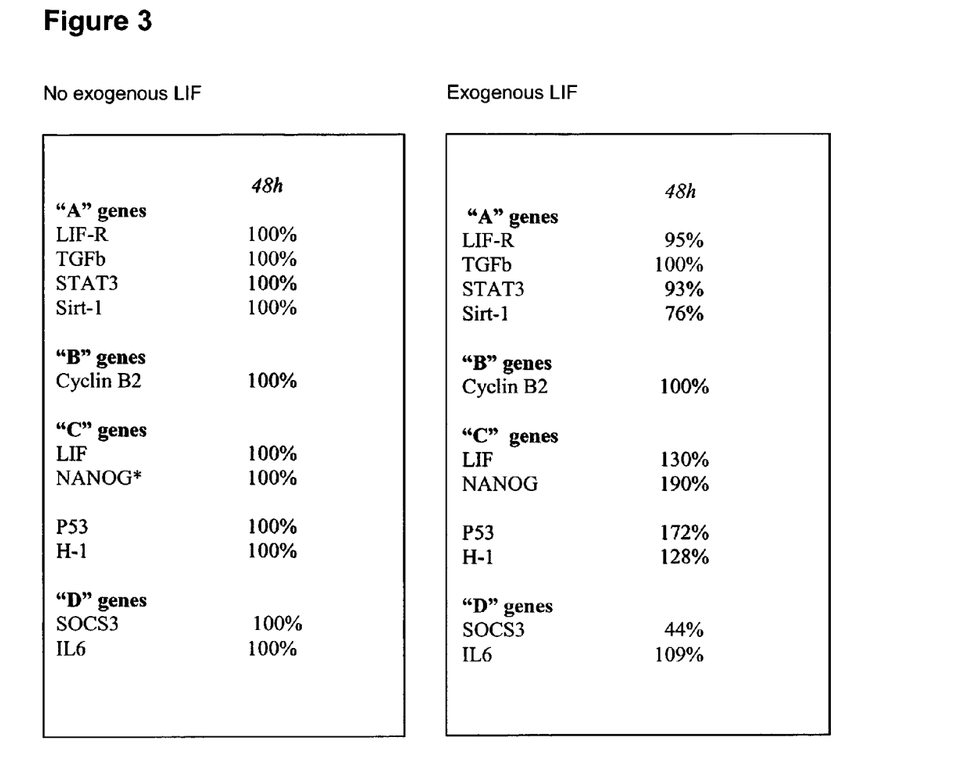
FIG. 3 shows the results of an experiment in which genetically normal mouse spleen cells were activated by CD3/CD28 ligation in the presence or absence of exogenous LIF.

Genetically normal mouse spleen cells cultured in serum-free growth medium were activated by anti-CD3 and anti-CD28 in the presence or absence of 10 ng/ml LIF. As shown in FIG. 3, at 48 h exogenous LIF was found to have increased expression of Nanog, p53, and LIF genes, and decreased SOCS-3 gene expression.

It is therefore predicted that in vivo therapy using targeted delivery of LIF will similarly increase the expression of Nanog, p53, and LIF genes in a target cell, and depress SOCS-3 expression.

Example 3

This Example shows that cell-derived LIF protein is linked to allo-tolerance, whereas release of IL6 protein is linked to allo-rejection.

Figure 4:
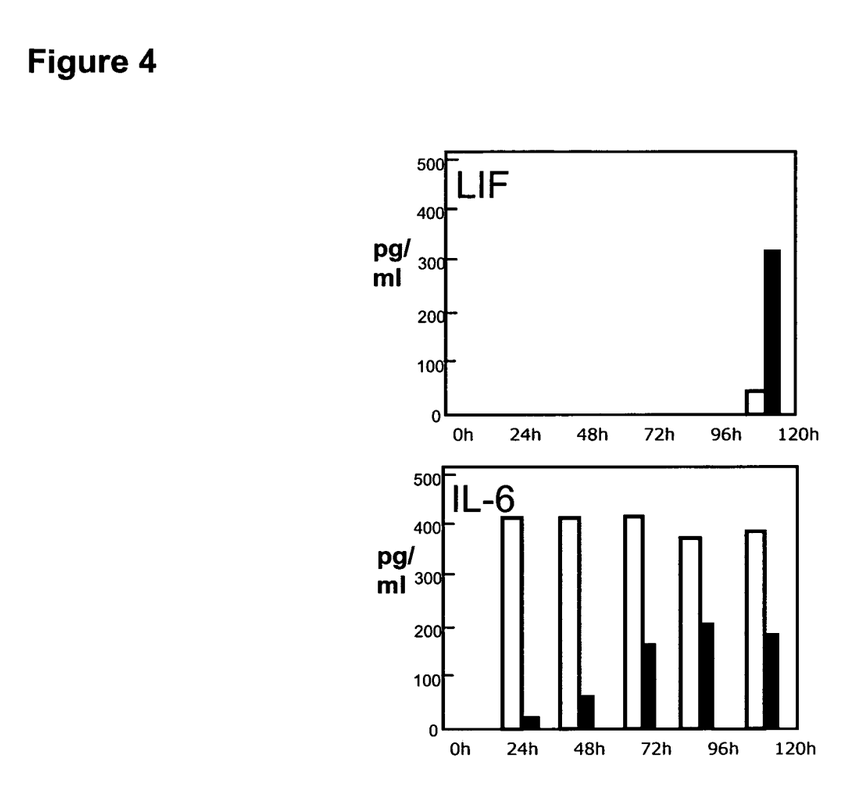
FIG. 4 shows the results of an experiment in histogram format in which spleen cells from in vivo primed allo-tolerant mice stimulated with donor antigen (black bars) display increased levels of LIF protein and decreased levels of IL6 protein when compared to spleen cells from in vivo primed allo-rejected mice stimulated with donor antigen (white bars), indicating that LIF protein is linked to allo-tolerance and IL6 protein is linked to allo-rejection.

Spleen cells from in vivo primed allo-tolerant, or allo-rejected, mice stimulated by donor antigen (i.e. irradiated donor-type spleen cells) in RPM' growth medium containing 10% FCS revealed that release of cell-derived LIF protein is linked to allo-tolerance, whereas release of IL6 protein is linked to allo-rejection (see FIG. 4).

It is therefore predicted that targeted delivery of LIF to CD4+ T cells in vivo will result in increases in the regulatory tolerant (Treg) lineage, whereas targeted delivery of IL6 will oppose induction of tolerance.

Conclusion

The invention represents a highly innovative approach to treatment of immune-mediated disease using targeted LIF therapy. The experiments incorporate two major advances of central relevance to treatment of immune-mediated indications, i.e. targeting plus harnessing of a natural tolerogenic pathway, and thereby underpin development of new and successful clinical therapies.

REFERENCES

Chen, Z. K., Cobbold, S. P., Waldmann, H. & Metcalfe, S. M. (1996) Amplification of natural regulatory immune mechanisms for transplantation tolerance. *Transplantation* 62, 1200-1206.

Fahmy T, Samstein R M, Harness C and Saltzman W M. (2005) Sustained target presentation in biodegradable polymers by surface modification with fatty acid conjugates *Biomaterials,* 26, 5727-36.

Fahmy T (2005) Targeted for drug delivery *Materials Today,* 8, 18-26.

Hilton D J, Nicola N A, Waring P M, Metcalf D. Clearance and fate of leukemia-inhibitory factor (LIF) after injection into mice *J Cell Physiol.* 1991 September; 148(3):430-9

Hori, S., Nomura, T. & Sakagushi, S. (2003) Control of regulatory T cell development by the transcription factor Foxp3. *Science* 299, 1057-1061.

Metcalfe S M, Tracy J Watson, Sandra Shurey, Elizabeth Adams, and Colin J. Green (2005) Leukaemia Inhibitory Factor (LIF) is linked to regulatory transplantation tolerance *Transplantation* 79, 726-730

Muthukumarana, Wook-Jin Chen, Stephen Maher, Bruce R. Rosengard, Alfred L. M. Bothwell and Su M Metcalfe (2007) Regulatory Transplantation Tolerance and "Stemness": evidence that Foxp3 may play a regulatory role in SOCS-3 gene transcription *Transplantation* 2007 (in press)

Muthukumarana, G E Lyons, Y Miura, L Thompson, T Watson, C J Green, S Shurey, A D Hess, B R. Rosengard, Su M. Metcalfe. Evidence for functional inter-relationships between FOXP3, leukaemia inhibitory factor, and axotrophin/MARCH-7 in transplantation tolerance *International Immunopharmacology* 6 (2006) 1993-2001

The invention claimed is:

1. A method of promoting an immune tolerance response in a patient, the method comprising administering to the patient a therapeutically effective amount of a composition comprising a plurality of biodegradable polylactidecoglycolide (PLG) polymer nanoparticles, wherein said PLG nanoparticles comprise a monoclonal antibody to CD4 as a targeting moiety that is able to bind selectively to the surface of a T lymphocyte cell, and wherein said PLG nanoparticles encapsulate leukaemia inhibitory factor (LIF).

2. The method of claim 1, wherein the patient is the recipient of, or intended to be the recipient of, transplanted tissue.

3. The method of claim 1, wherein administering to the patient a therapeutically effective amount of a composition comprising said PLG nanoparticles comprises pretreating a donor tissue with said PLG nanoparticles prior to introducing said donor tissue and said PLG nanoparticles into the patient.

* * * * *